United States Patent [19]
Born

[11] Patent Number: 5,608,746
[45] Date of Patent: Mar. 4, 1997

[54] METHOD FOR AVOIDING EYE DAMAGE WHEN USING HIGH-POWER LASERS

[75] Inventor: Gunthard Born, Munich, Germany

[73] Assignee: Deutsche Aerospace AG, Munich, Germany

[21] Appl. No.: 272,758

[22] Filed: Jul. 11, 1994

[30] Foreign Application Priority Data

Jul. 27, 1993 [DE] Germany .................. 43 25 139.0

[51] Int. Cl.⁶ ........................................ H01S 3/10
[52] U.S. Cl. .............. 372/33; 362/109; 362/111
[58] Field of Search ............ 372/33; 362/109–114; 356/3; 250/236; 606/5

[56] References Cited

U.S. PATENT DOCUMENTS 5,152,759  10/1992  Parel et al. .................. 606/5
5,321,259   6/1994  Morgan ...................... 250/236

OTHER PUBLICATIONS

*International Defense Review* entitled "Laser Protection for AFVs: the eyes have it" by Murray Hammick, Aug. 1991, pp. 818–821.

*Wehrtechnik* entitled "Militärische Laser werden augensicher" by Klaus Müller, wt Jan. 1987, pp. 55–62.

*Wehrtechnik* entitled "Flugabwehr durch Hochenergielaser" by Erhard Heckmann, wt Dec. 1985, pp. 77–80.

*Armed Forces Journal* entitled "Hand–Held Laser Weapons Are Waiting in the Wings" by Maj. Gen. Bengt Anderberg and Dr. Myron L. Wolbarsht, May 1992, pp. 60 and 61.

*Primary Examiner*—Brian Healy
*Assistant Examiner*—Yisun Song
*Attorney, Agent, or Firm*—Evenson, McKeown, Edwards & Lenahan, P.L.L.C.

[57] ABSTRACT

A method for avoiding damage to the eyes when using high-power lasers in the eye-transmissible spectral region is provided. By adding a laser or a radiation in the visible spectral region, the intensity of the radiation is increased as a function of time in the shape of a ramp from zero to higher values which lead to a conscious or reflex-type closing of the eyelids This therefore prevents the eyes from being damaged by the subsequent high-power laser beam.

15 Claims, 1 Drawing Sheet

METHOD FOR AVOIDING EYE DAMAGE WHEN USING HIGH-POWER LASERS

BACKGROUND AND SUMMARY OF THE INVENTION

This invention relates to a method for avoiding eye damage when using high-power lasers and, more particularly to a method for avoiding eye damage when using high-power lasers operating in the spectral region which is transmissible for the eye lens. One such known method is described, for example, from the publications *International Defence Review*", 8/1991, pp. 818–821, and *Wehrtechnik, wt* 1/87, pp. 55–62.

It has heretofore been known to have laser systems which have to master the various tasks in civil as well as military fields of application. These tasks include, for example, laser range finding equipment, laser Doppler radar systems, laser target illuminating and marking equipment, laser systems for the analysis of the atmosphere as well as systems with very high laser power which have as their object an interference with, but also a destruction of, the radiated material.

From the publication *Wehrtechnik, wt* 12/85, Pages 77 to 80, a system of very high laser power with the object of destroying the radiated material is known. The lasers used for the abovementioned applications operate in spectral regions for which the atmosphere is basically transmissible under good and fair weather conditions, as indicated in the graph of FIG. 1. These lasers particularly include the deuterium fluoride laser in the 3–5 μm spectral region, the $CO_2$-laser in the 10 μm spectral region, the neodymium laser (Nd) in the close infrared region at 1.06 μm and additional lasers which operate at different wavelengths in these spectral regions achieved by the doubling or Raman shift of their output frequency.

Particularly, the high-power laser systems which have the purpose of destroying military objects as a result of the thermal effect of the absorbed laser radiation have the characteristic of temporarily interfering with or permanently destroying, over very long distances, sensors which operate in the spectral region of the laser. Corresponding to their purpose, the sensors must be highly sensitive.

From the publication *Armed Forces Journal*, May 1992, pp. 60 et. seq., laser systems are known which have the purpose of eliminating sensors either by an effective interference or by destruction. Lasers which are suitable for this purpose are, for example, $CO_2$-lasers and DF-lasers for heating imaging equipment which operate in the above-mentioned infrared bands, and the Nd-laser which—invisible to the human eye—emits at a wavelength 1.06 μm and is also used with double frequency (wavelength 0.53 μm) and can, therefore, be used for temporarily blinding human beings.

Because of the fact that meteorological conditions change significantly, thus affecting the reducing characteristics of the atmosphere, and because the distance to the target is frequently unknown, it is possible, however, only in rare cases to apportion the emitted laser power in the visible spectral region in such a manner that, although a temporary blinding will occur, there will now be destruction of the retina.

Nd-lasers, which do not operate by means of a double frequency, but rather by means of the base frequency and a wavelength at 1.06 μm, are not visible at all. However, similarly to the visible frequency-doubled radiation, they are focussed at 1.06 μm on the fundus of the eye and therefore destroy even at a relatively low occurring energy density the radiated point of the fundus of the eye without any possibility for the affected human being to react ahead of time.

There is therefore needed a method by which the danger of permanent eye damage to the operator or the observer of a high-power laser is eliminated, but which permits the unimpaired implementation of the tactical mission, for example, the destruction of a sensor.

These needs are met by a method for avoiding eye damage when using high-power lasers operating in the spectral region which is transmissible for the eye lens. A warning laser which operates in the visible region is assigned to the beam of the high-power laser. The power of the warning laser, within a short warning period, is increased from zero to increasingly higher values before the laser beam of the high-power laser reaches the eye.

Other objects, advantages and novel features of the present invention will become apparent from the following detailed description of the invention when considered in conjunction with the accompanying drawings.

DETAILED DESCRIPTION OF TEE DRAWINGS

The invention largely or completely eliminates the danger of permanent damage to the eyes during the use of high-power lasers. This is accomplished by the fact that a so called "warning laser" is assigned to lasers which operate in the spectral region (approximately 0.35 μm to 1.4 μm) that is transmissible for the human eye. The warning laser operates in the visible spectral region of between approximately 0.4 μm and 0.75 μm. The warning laser's power is increased during a warning period of approximately one to several tenths of a second in the shape of a ramp (FIG. 3) from a zero value to values that are so high as to ensure that the-human being who, after the application, is necessarily or accidentally within the beam path, will consciously or instinctively close their eyes because of the lid closure reflex of the eyes or turn away. However, it is important that the high power value, for which the laser system is designed, for example for the destruction of video or low-light level amplifier cameras, is switched on only after the above-mentioned warning time of a few tenths of a second.

On the other hand, the warning time of less than a second is short enough that the involved person at the apparatus to be destroyed will not have time to protect the radiated apparatus. Only his eye reflex will be activated. During this short time period, the operator can neither move the radiated apparatus out of the beam, nor cover it in any manner, nor rotate it to zones of its structure which are not endangered.

In each case, the above-described method therefore meets its operative objective, but, at the same time, prevents eye injuries that are superfluous to this objective.

As an additional measure, the warning period is selected to be longer than the average fluctuation time of the laser radiation at the receiver which is caused by atmospheric turbulence.

Figure 1:
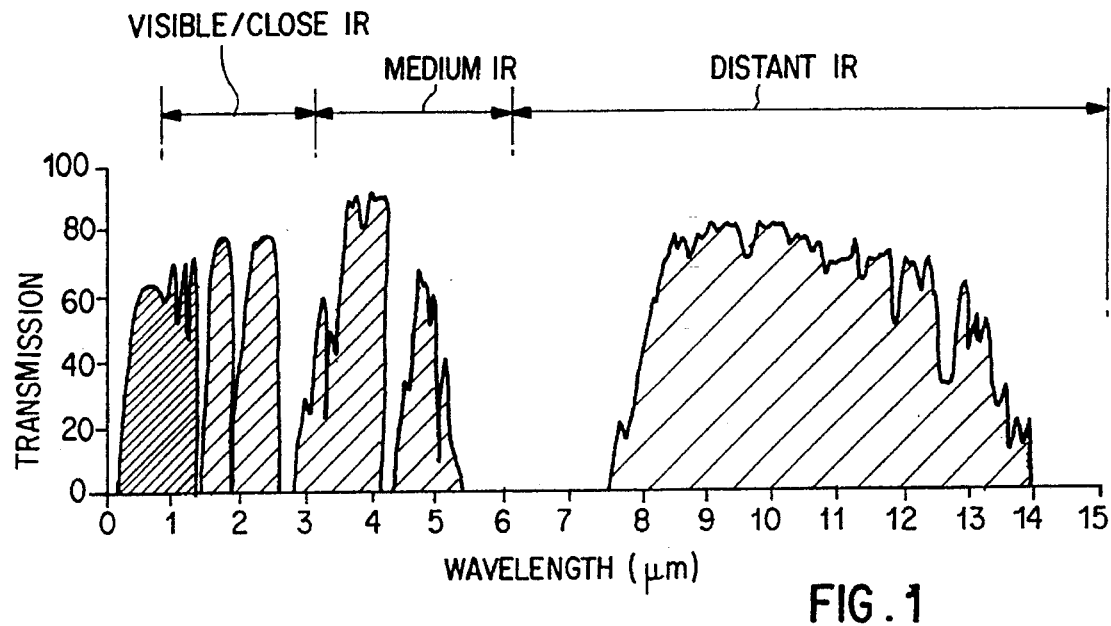
FIG. 1 is a graphical diagram of the transmission in the atmosphere of the individual wavelengths in the visible and individual IR-regions.
Figure 2:
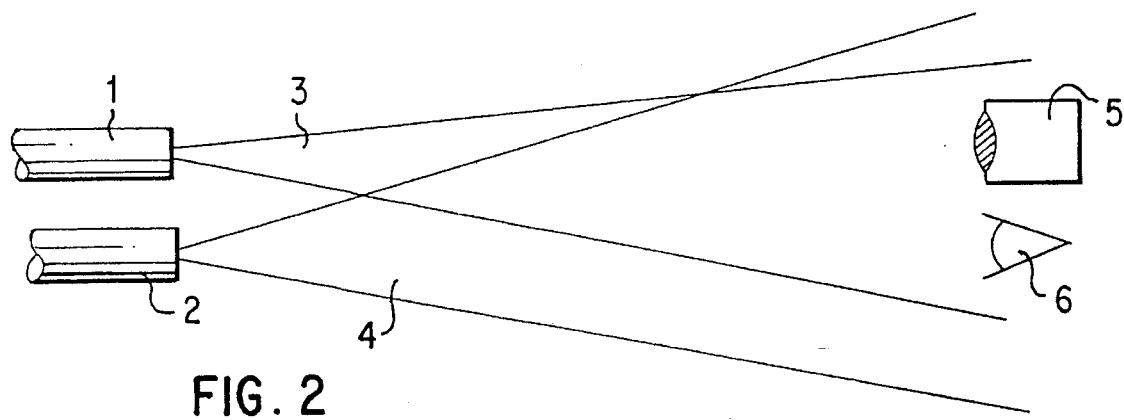
FIG. 2 is a schematic diagram of the construction and the operation of an embodiment of the present invention.

One preferred embodiment provides a frequency-doubled Nd-laser, preferably an Nd-YAG-laser, as the warning laser 2 (FIG. 2). In a further development of this embodiment, it is preferred to operate the Nd-YAG-laser such that, in a first phase, it beams in a frequency-doubled manner with an increasing power—and is therefore used as the warning laser—and in a second phase emits its total high-power laser radiation, thus operating as a destroying laser, etc.. In this second phase, the laser also is usable at its base wavelength.

A further preferred embodiment provides that a laser system is formed which, in addition to the Nd-YAG-laser 1 with its combatting high-power beam 3 and the warning beam 4, has one or several lasers which simultaneously carry out the destruction of sensors in one or several infrared spectral bands on the other side of the wavelength of 1.06 µm.

In a still further embodiment, a warning laser 2 is used whose beam 4 has a spatial coherence which is low in comparison to the diffraction-limited beam. In this case, the beam spread is, for example, up to one order of magnitude larger than that of a diffraction-limited beam. This has the result that, while the brightness sensation is the same, the beam-caused stress to the retina is lower and the danger of injuring the observer 6 is therefore reduced.

Figure 3:
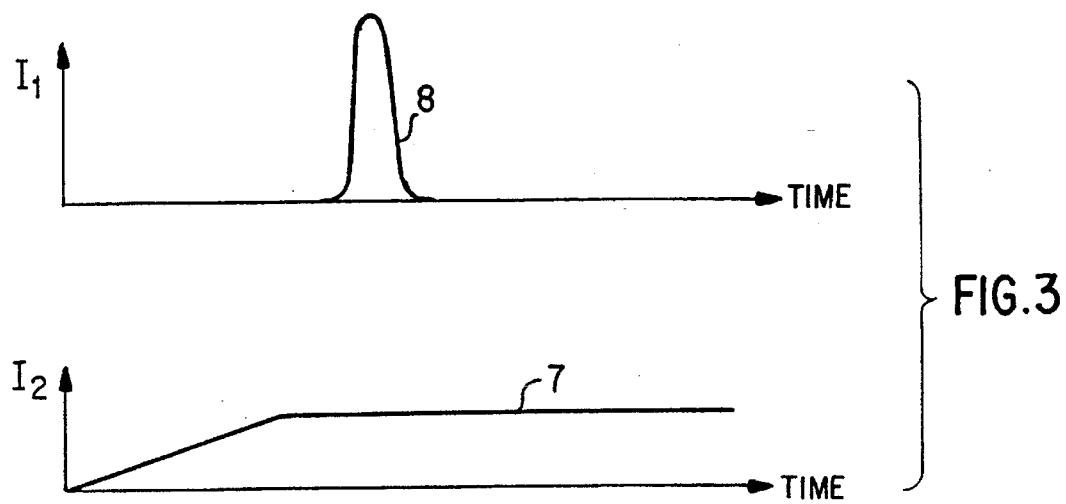
FIG. 3 is a graphical diagram comparison of the laser beams according to the embodiment of FIG. 2.

In FIGS. 2 and 3, the reference number 1 indicates the high-power laser system and the reference number 2 indicates the warning laser. As mentioned above, an Nd-YAG-laser, for example, may at the same time serve as a high-power combatting laser and a warning laser. In this case, the combatting laser beam 3 and the warning laser beam 4 originate from a single laser. The sensor, which is selected, for example, as the target to be combatted, has the reference number 5, while the respective endangered eye of an observer has the reference number 6. In the diagram of FIG. 3, the variation in time for the intensity $I_2$ of the warning laser beam 4 has the reference number 7 and that for the intensity $I_1$ of the beam 3 has the reference number 8.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A method for avoiding eye damage in the use of a high-power laser operating in a spectral region transmissible for an eye lens, the method comprising the steps of:
   assigning a warning laser to a beam of said high-power laser, said warning laser operating in the visible region; and
   increasing the power of a warning laser beam of said warning laser from a zero value to increasingly higher values within a short warning period during which said warning laser beam is imaged on said eye lens to activate a lid closure reflex before said laser beam of the high-power laser reaches said eye lens.

2. A method according to claim 1, further comprising the step of: selecting said short warning period to be longer than an average fluctuation time of the laser radiation caused by atmospheric turbulence at a receiver of said beam.

3. A method according to claim 1, wherein said warning laser is a frequency-doubled Nd-laser.

4. A method according to claim 2, wherein an Nd:YAG-laser operates as said warning laser, in a first phase, in a frequency-doubled manner with an increasing power and, in a second phase, is operated as said high-power laser at its full power.

5. A method according to claim 3, wherein an Nd:YAG-laser operates as said warning laser, in a first phase, in a frequency-doubled manner with an increasing power and, in a second phase, is operated as said high-power laser at its full power.

6. A method according to claim 4, further comprising the step of: assigning at least one laser which carries out the destruction of optical sensors in other infrared spectral regions to said Nd:YAG-laser which is used as both said warning and high-power laser.

7. A method according to claim 5, further comprising the step of: assigning at least one laser which carries out the destruction of optical sensors in other infrared spectral regions to said Nd:YAG-laser which is used as both said warning and high-power laser.

8. A method according to claim 4, wherein said Nd:YAG-laser has a beam with a lower spatial coherence in the first phase than in the second phase.

9. A method according to claim 5, wherein said Nd:YAG-laser has a beam with a lower spatial coherence in the first phase than in the second phase.

10. A method for avoiding eye damage in the use of a high-power laser operating in a spectral region transmissible for an eye lens, the method comprising the steps of:
    assigning a warning laser to a beam of said high-power laser, said warning laser operating in the visible region;
    increasing the power of a warning laser beam of said warning laser from a zero value to increasingly higher values within a short warning period during which said warning laser beam is imaged on said eye lens before said laser beam of the high-power laser reaches said eye lens; and
    wherein an Nd:YAG-laser operates as said warning laser, in a first phase, in a frequency-doubled manner with an increasing power and, in a second phase, is operated as said high-power laser at its full power.

11. A method according to claim 10, further comprising the step of: assigning at least one laser which carries out the destruction of optical sensors in other infrared spectral regions to said Nd:YAG-laser which is used as both said warning and high-power laser.

12. A method according to claim 10, wherein said Nd:YAG-laser has a beam with a lower spatial coherence in the first phase than in the second phase.

13. A laser system for destroying objects while avoiding eye damage to an operator of said objects, comprising:
    a high-power laser operating in a spectral region transmissible for an eye lens of said operator;
    a warning laser operating in one of a visible and close-infrared region, said warning laser being assigned to a beam of said high-power laser;
    wherein said warning laser operates within a short warning period to increase from zero to subsequently higher values before said beam of said high-power laser reaches said eye lens; and
    wherein both said high-power laser and said warning laser are formed from a single Nd:YAG-laser operating in two phases, said first phase being said warning laser wherein the Nd:YAG-laser operates in a frequency-doubled manner with increasing power and, wherein in said second phase it operates as the high-power laser.

14. A laser system for destroying objects while avoiding damage to an eye of an operator of said objects, comprising:
    a high-power laser operating in a spectral region transmissible for an eye lens of said operator;
    a warning laser operating in visible region, said warning laser being assigned to a beam of said high-power laser;
    wherein said warning laser operates within a short warning period, during which a warning laser beam of the warning laser is imaged on said eye, to increase from zero to subsequently higher values to activate a lid closure reflex before said beam of said high-power laser reaches said eye lens.

15. A laser system according to claim 14, wherein said warning laser is a frequency-doubled Nd-laser.

* * * * *